United States Patent [19]

Borschneck

[11] Patent Number: 4,608,971
[45] Date of Patent: Sep. 2, 1986

[54] EMERGENCY LEG SPLINT

[76] Inventor: Anthony G. Borschneck, 15603 Prospect Dr., Redding, Calif. 96001

[21] Appl. No.: 755,634

[22] Filed: Jul. 16, 1985

[51] Int. Cl.[4] ............................................. A61F 5/04
[52] U.S. Cl. .................................... 128/85; 128/84 C
[58] Field of Search ..................... 128/87 R, 84 C, 85, 128/89 R

[56] References Cited

U.S. PATENT DOCUMENTS

| 350,526 | 10/1886 | Bunce | 128/85 |
|---------|---------|-------|--------|
| 739,200 | 9/1903 | Moore | 128/85 |
| 850,610 | 4/1907 | Ward | 128/85 |
| 1,238,224 | 8/1917 | Vickers | 128/85 |
| 3,756,227 | 9/1973 | Sager | 128/85 |

Primary Examiner—Stephen F. Husar
Attorney, Agent, or Firm—Lothrop and West

[57] ABSTRACT

A splint for a human patient's leg, especially for emergency use, has a housing tube and a base tube telescoped for length adjustment. A holder secures a selected length. A base bar on the end of the base tube fits approximately against the patient's ischial tuberosity. An ankle tube telescopes on the housing tube and is movable against the tension of a spring at one end anchored within and to the housing tube. The outer end of the spring is joined by a cable to the ankle tube after passing around a pulley within and journalled in the housing tube. An ankle bar extends transversely on the end of the ankle tube and does not project from but lies well within the outline or compass of the patient. Suitable cravat loops are provided on the base bar and on the ankle bar. An operating handle assists in displacing the ankle tube and the housing tube to adjust the tension of the spring to an indicated amount.

13 Claims, 7 Drawing Figures

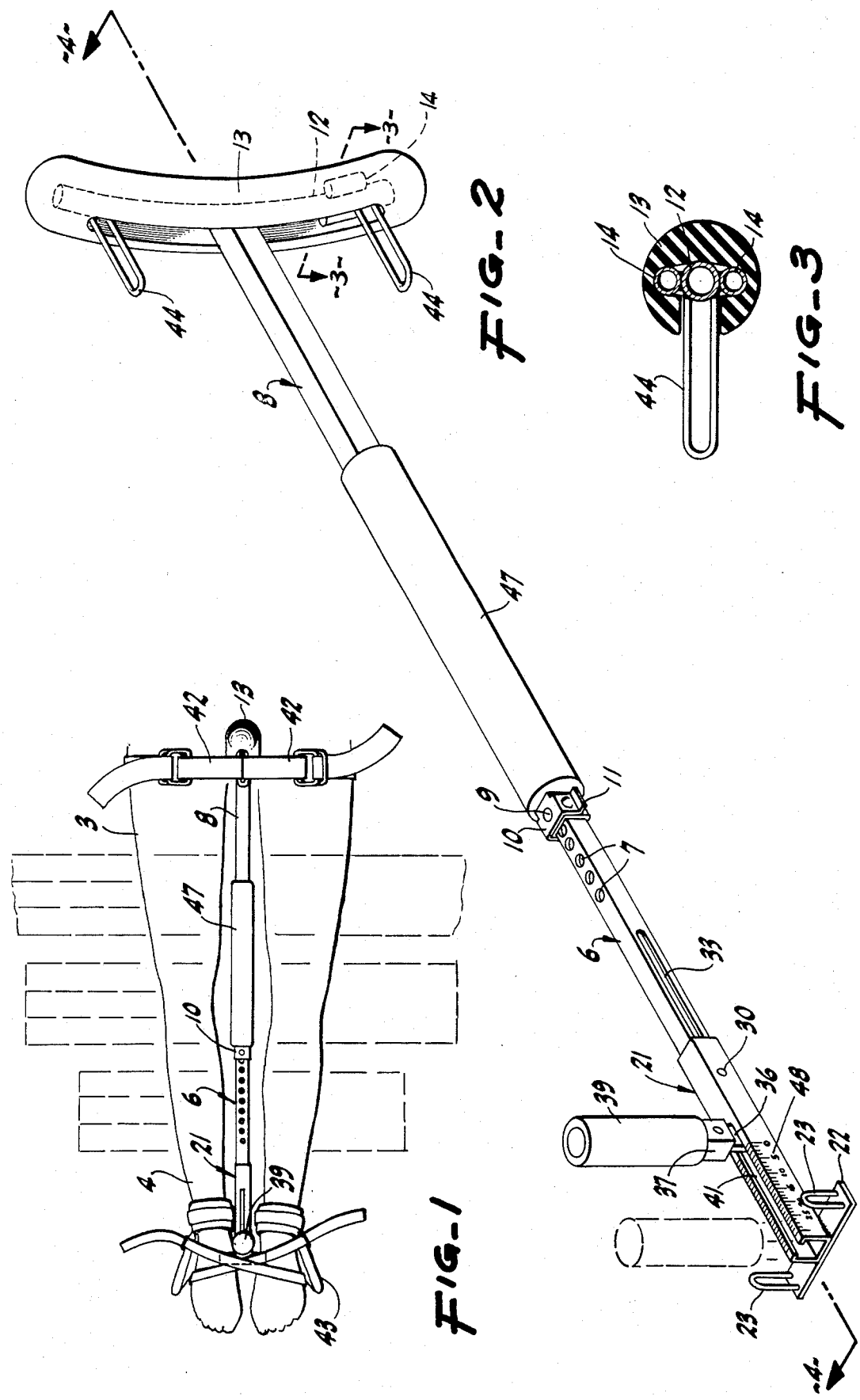

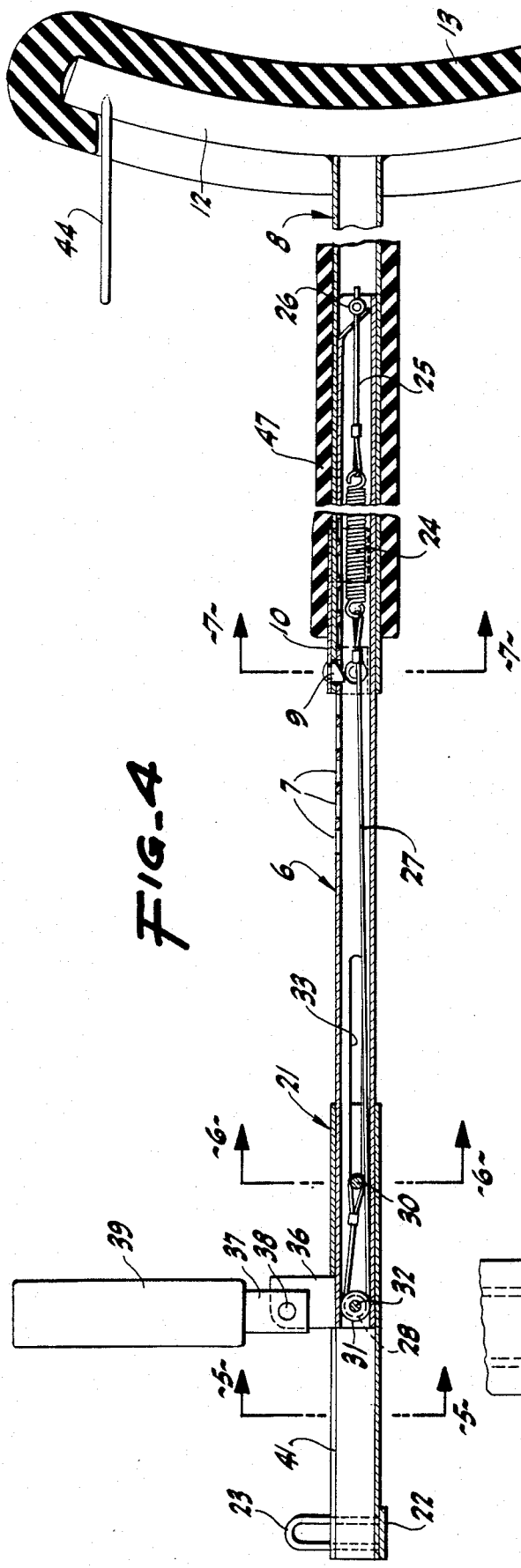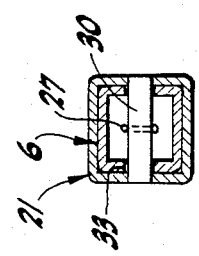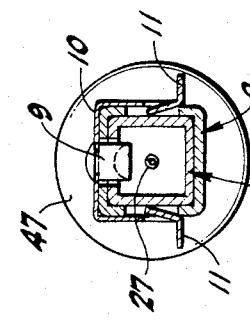

EMERGENCY LEG SPLINT

BACKGROUND OF THE INVENTION

The field of the invention has to do with appliances for use in assisting patients with broken legs, particularly, and is primarily designed for emergency use under conditions wherein transport and the like for an injured person from a remote area to a hospital may be under trying and restricted circumstances.

Related art is represented by the following publications:

U.S. Pat. Nos. 3,859—Post, Dec. 16, 1844, 350,526—Bunce, Oct. 12, 1886, 739,200—Moore, Sept. 15, 1903, 850,610—Ward, Apr. 16, 1907, 1,238,224—Vickers, Aug. 28, 1917, 2,269,065—Roberts, Jan. 6, 1942, 2,529,786—Shaw, Nov. 14, 1950, 3,580,248—Larson, May 25, 1971, 3,756,227—Sager, Sept. 4, 1973, 3,942,521—Klippel, Mar. 9, 1976, 4,350,153—Borschneck, Sept. 21, 1982.

The EMT Journal, St. Louis, Volume 4, No. 1, pages 42–47, March 1980

The C. V. Mosby Company, article entitled "Sager Emergency Traction Splint: A New Splinting Device For Lower Limb Fractures" by Borschneck and Wayne JEMS for March 1981, Volume 6, No. 3, article entitled "Traction Splinting" by Thom Dick on pages 26–36.

SUMMARY

A spring, pulley and cable structure entirely mounted and enclosed in telescopic housing and anchor tubes provides a leg splint affording an adjustable force between a base bar seated against the user's ischial tuberosity and an ankle cravat secured to the user's ankle. The splint lies alongside the inside of the user's leg and does not project beyond his foot.

BRIEF DESCRIPTION OF THE DRAWINGS

FIG. 1 is a plan of a leg splint constructed in accordance with the invention shown in a typical use position.

FIG. 2 is an isometric perspective showing the mechanical construction of the splint.

FIG. 3 is a cross-section, the plane of which is indicated by the line 3—3 of FIG. 2.

FIG. 4 is a cross-section, the plane of which is indicated by the line 4—4 of FIG. 2.

FIGS. 5, 6 and 7 are cross-sections, the planes of which are indicated by the respective lines 5—5, 6—6 and 7—7 of FIG. 4.

DESCRIPTION OF THE PREFERRED EMBODIMENT

Especially for use with a patient 3 who has suffered a fractured bone in his leg 4 and is available lying on the ground, for example, there is especially provided a splint in accordance with the present improved structure. Particularly employed is a housing tube 6, preferably of rectangular or square cross-section, provided in one wall with a number of spaced-apart apertures 7 to cooperate with and to telescope within a base tube 8. This is likewise of square cross-section and makes a relatively close but freely sliding fit with the tube 6. Such sliding may be restrained by a spring-pressed detent 9 mounted in a spring clip 10 fast on the tube 8 and having appropriate finger-operated projections 11. The detent 9 is beveled on one side for allowing free tube telescoping in one direction and for holding the tubes 6 and 8 against sliding in the opposite direction.

The base tube 8 extends to a cross or base bar 12 conveniently of an arcuate shape removably carrying a rather large foam rubber pad 13 positioned against rotation and shifting on the bar 12 by extensions 14 from the bar 12 so that the bar, and particularly the padding 13, can readily be seated adjacent to and bear against the ischial tuberosity of the patient.

With this arrangement, it is possible to position the cross bar 12 against the patient very quickly and then by momentarily releasing the spring detent 9 adjust or telescope the tubes 6 and 8 with respect to each other far enough to adjust the overall length of the splint to accommodate the size of the particular patient. This adjustment is preferably of sufficient extent so that adults and children can be accommodated by the same device.

Also telescoped on the housing tube 6 is an ankle tube 21 likewise of generally rectangular configuration and of a size to engage slidably and fit easily over the tube 6. The ankle tube 21 in the vicinity of the user's ankle carries a relatively flat ankle bar 22 that extends transversely, readily to accommodate a pair of outstanding cravat loops 23.

Means are provided for yieldably positioning the ankle bar 22 with respect to the base bar 12.

At a convenient point well within and housed by the housing tube 6 there is disposed a helical tension spring 24 having a cable 25 fastened to a securing device 26 resting against an inturned wall of the tube 6. One end of the spring 24 is thus held virtually immovable with respect to the housing tube 6. The spring has considerable room for extension within such tube. At its other end, the spring 24 is connected to a cable 27, proceeding farther through the housing tube and trained around and lying in a central groove 28 in a pulley 29. The cable 27, after rounding the pulley 29, is terminated by a loop engaging a cross pin 30 extending through longitudinal side cut-outs 33 in the housing tube 6. The pin 30 is fast in the ankle tube 21. The pulley 29 revolves on a shaft 32 mounted in the side walls of the housing tube 6. To keep the cable 27 in place, the pulley 29 includes pulley wheels 31 of a diameter nearly that of the interior of the housing tube 6 so that the cable is confined laterally and radially within the groove 28.

Protruding from the end of the tube 6 is a fastening plate 36 supporting a channeled handle lever 37 by means of a pivot pin 38. A soft wrap 39 is positioned around the lever 37. The lever 37 can stand in an upright stop position or can be folded down for compactness when necessary. A groove 41 in the upper face of the tube 21 allows for the lever 37 during relative motion of the ankle tube 21 and the housing tube 6.

A number of appropriate straps or bridle cravats 42 and 43 are employed. Additional cravats and straps (shown in available position by broken lines in FIG. 2) can likewise be utilized. The cravat or cravats 42 preferably engage loops 44 projecting from the base bar 12, whereas an ankle cravat or cravats 43 engage the loops 23.

In the use of this device, with the patient lying flat as shown in FIG. 1, the splint is positioned between the patient's legs with the padding 13 of the bar 12 preferably in substantial abutment with his ischial tuberosity.

The spring clip projections 11 are raised and the detent 9 is lifted out of the base tube 8. Alternatively, the housing tube 6 is simply pulled outwardly of the base tube 8 as permitted by the beveled detent 9. The tubes 6 and 8 are moved axially with respect to each other by the user pulling on the handle lever 37 and using a soft grip 47 around the tube 8. When the correct length has been established with the bar 22 adjacent the user's ankles and the detent 9 in one of the apertures 7, the cravats 43 disposed in the loops 23 are wrapped around one or both of the patient's ankles. A firm connection is thereby made between the cross bar 22 and at least the ankle of the injured leg.

Then the handle lever 37 is further drawn so as to tension the spring 24 and to move the ankle bar 22 farther away from the cross bar 12. When the desired distance between the opposite ends of the splint is imposed, the desired tension is transmitted to the user's leg. The amount of such displacement and tension is indicated by a traction scale 48 which lies in proximity to the edge of the lever 37, serving as a pointer. Any predetermined amount of displacement or force can be imposed, preferably a value of several pounds.

The cravat or cravats 42 and also other cravats are used to afford lashings around the patient's thigh and around the patient's leg below the knee or in any other locations deemed proper. In order to control rotation of the legs, a pedal binding, comprising a strap having a FIG. 8 configuration is applied to the feet.

When this application has been made, the limb is well immobilized and there is no projection of the splint beyond the bottom of the patient's foot. This ensures that the patient can be carried readily and in a proper position on a relatively short litter and can be put into a small evacuating helicopter or short pick-up automobile without danger of contact between the splint and the surroundings, because the splint ends within the patient's outline and does not project beyond his relaxed foot.

What is claimed is:

1. An emergency leg splint comprising a housing tube, means engaging one end portion of said housing tube for seating on the ischial tuberosity of a patient, an ankle tube movably projecting from the other end portion of said housing tube, a pulley rotatably mounted within said housing tube, a cable having two ends and trained around said pulley, a spring within said housing tube, means for connecting one end of said spring to said housing tube, means for connecting the other end of said spring to one end of said cable, and means for connecting the other end of said cable to said ankle tube.

2. A device as in claim 1 in which said means for engaging the ischial tuberosity includes a base tube in telescopic engagement with said housing tube.

3. A device as in claim 2 in which said housing tube has a plurality of apertures therein, and means on said base tube for selectively extending into any one of said apertures.

4. A device as in claim 2 including a base bar extending transversely across the end of said base tube for substantial conformance with said ischial tuberosity.

5. A device as in claim 4 including means on said base bar for receiving a bridle cravat.

6. A device as in claim 1 in which said ankle tube is in telescopic engagement with said housing tube.

7. A device as in claim 6 including an ankle bar at and extending transversely from the end of said ankle tube.

8. A device as in claim 7 including means on said ankle bar for receiving an ankle cravat.

9. A device as in claim 1 including means on said housing tube and on said ankle tube for indicating the relative positions thereof.

10. A device as in claim 1 including a lateral projection from said housing tube near an end thereof, and means defining a slot in said ankle tube receiving said projection and forming a stop for limiting the movement of said ankle tube relative to said housing tube.

11. A device as in claim 10 including a handle pivotally connected to said projection.

12. A device as in claim 1 in which said ankle tube defines the endmost portion of said splint.

13. A device especially for emergency use as a splint for a human patient's leg comprising a housing tube adapted to extend alongside the inner side of said leg, means connected to said housing tube to lie substantially in abutment with said patient's ischial tuberosity, an ankle tube telescopically engaging and movable relative to said housing tube and adapted to extend along the inner side of said leg in the vicinity of the ankle, means for use in strapping said housing tube to said leg, means for use in strapping said ankle tube to said patient's ankle, a tension spring within said housing tube, means for fastening one end of said tension spring to said housing tube, a pulley, means for mounting said pulley within said housing tube, a cable within said housing tube and trained around said pulley, and means for fastening one end of said cable to the other end of said spring and for fastening the other end of said cable to said ankle tube.

* * * * *